United States Patent
Belef

(10) Patent No.: US 6,485,482 B1
(45) Date of Patent: Nov. 26, 2002

(54) ROTATIONAL AND TRANSLATIONAL DRIVE COUPLING FOR CATHETER ASSEMBLY

(75) Inventor: W. Martin Belef, San Jose, CA (US)

(73) Assignee: Scimed Life Systems, Inc., Maple Grove, MN (US)

(*) Notice: Subject to any disclaimer, the term of this patent is extended or adjusted under 35 U.S.C. 154(b) by 87 days.

(21) Appl. No.: 09/620,642

(22) Filed: Jul. 21, 2000

Related U.S. Application Data

(60) Provisional application No. 60/146,609, filed on Jul. 30, 1999.

(51) Int. Cl.[7] ............................................. A61M 25/01
(52) U.S. Cl. ..................... 604/528; 606/108; 606/159; 604/164.08
(58) Field of Search ................................ 606/108, 159, 606/167, 180; 604/95.01, 164.01, 164.08, 264, 523, 528

(56) References Cited

U.S. PATENT DOCUMENTS

| | | | |
|---|---|---|---|
| 5,827,313 A | * 10/1998 | Ream | 606/171 |
| 5,919,161 A | * 7/1999 | Hill et al. | 604/95.01 |
| 6,193,736 B1 | * 2/2001 | Webler et al. | 606/171 |
| 6,319,227 B1 | * 11/2001 | Ruiz | 604/95.01 |

FOREIGN PATENT DOCUMENTS

| | | |
|---|---|---|
| DE | 4344312 A1 | 7/1994 |
| WO | WO 94/0052 | 1/1994 |
| WO | WO 98/12967 | 4/1998 |
| WO | WO 99/56627 | 11/1999 |

\* cited by examiner

Primary Examiner—Glenn K. Dawson
(74) Attorney, Agent, or Firm—Townsend and Townsend and Crew LLP

(57) ABSTRACT

A driven catheter system (2) includes broadly a driven catheter assembly (6) coupled to a control unit (4). The driven catheter assembly includes a motor drive unit (8) and a catheter assembly (10) mounted thereto. The catheter assembly includes a rotational and translational drive coupling (26) and a catheter (14) extending therefrom. The catheter includes a sheath (16) and a core (18) slidably housed within the sheath. The drive coupling includes an elongate rotary drive element (36), defining a first longitudinal drive path, mounted for rotation about a longitudinal axis (42). A termination element (44) is mounted to the proximal end of the core and slides along the first longitudinal drive path but rotates with the rotary drive element. A bearing (46) has an inner race (48) secured to the termination member and an outer race (50) coupled to the longitudinal drive element (54, 62) of a longitudinal driver (56). Rotation of the rotary drive element rotates the termination element and the proximal end of the core therewith about the longitudinal axis. Longitudinal movement of the longitudinal drive element translates the bearing parallel to the longitudinal drive path; this causes the termination element and the proximal end of the core therewith to be translated along the first longitudinal drive path, the translational and rotational movements being independent of one another.

24 Claims, 3 Drawing Sheets

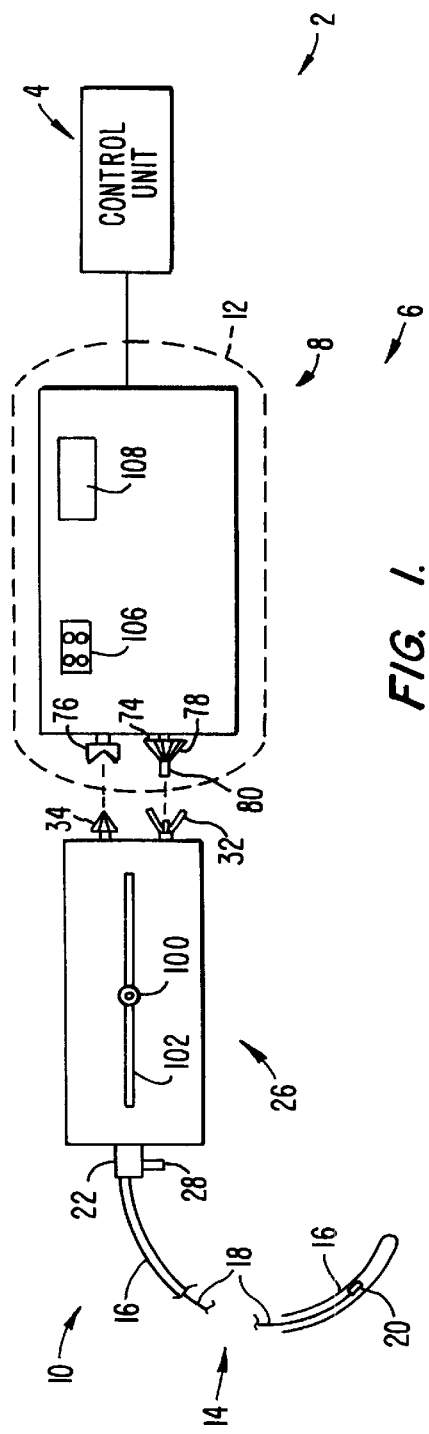
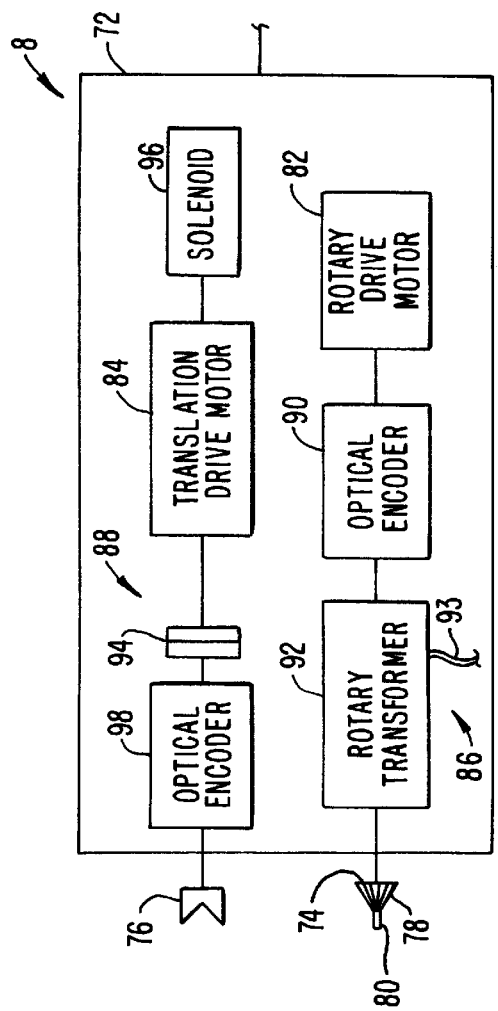
FIG. 1.
FIG. 4.

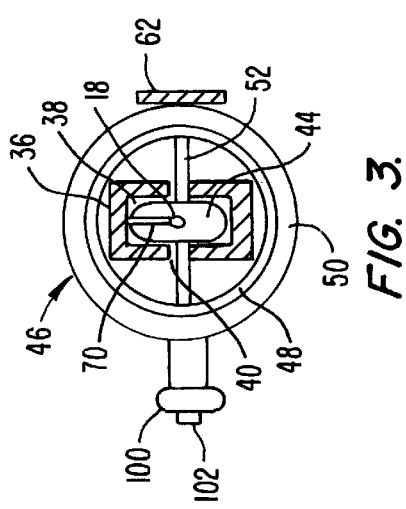
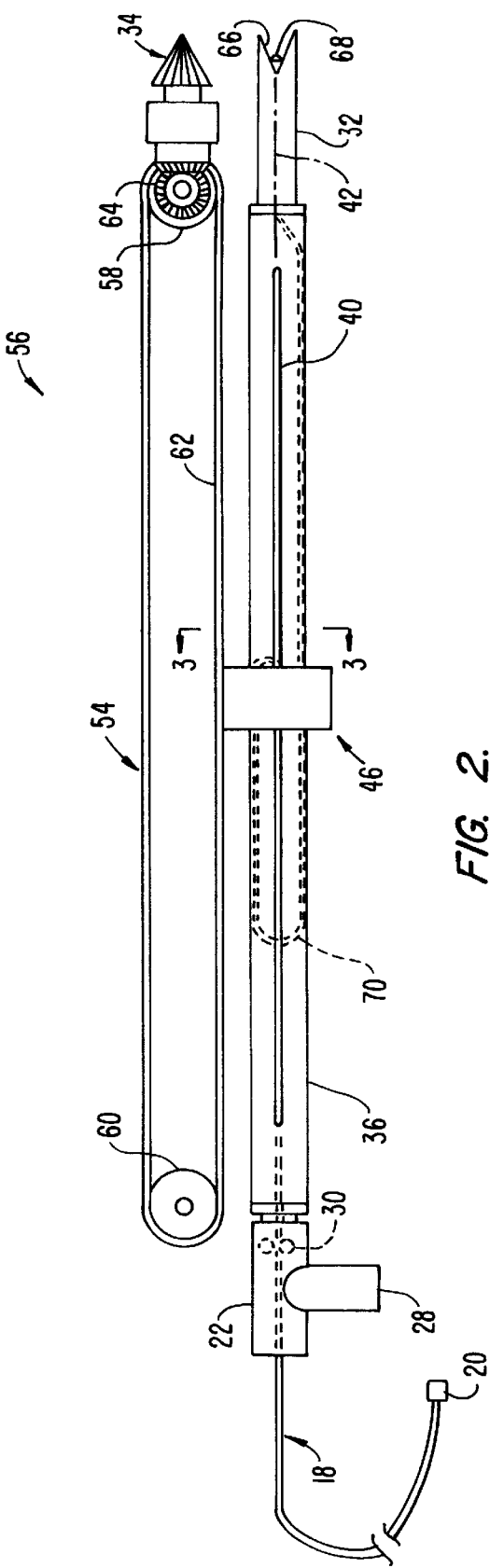

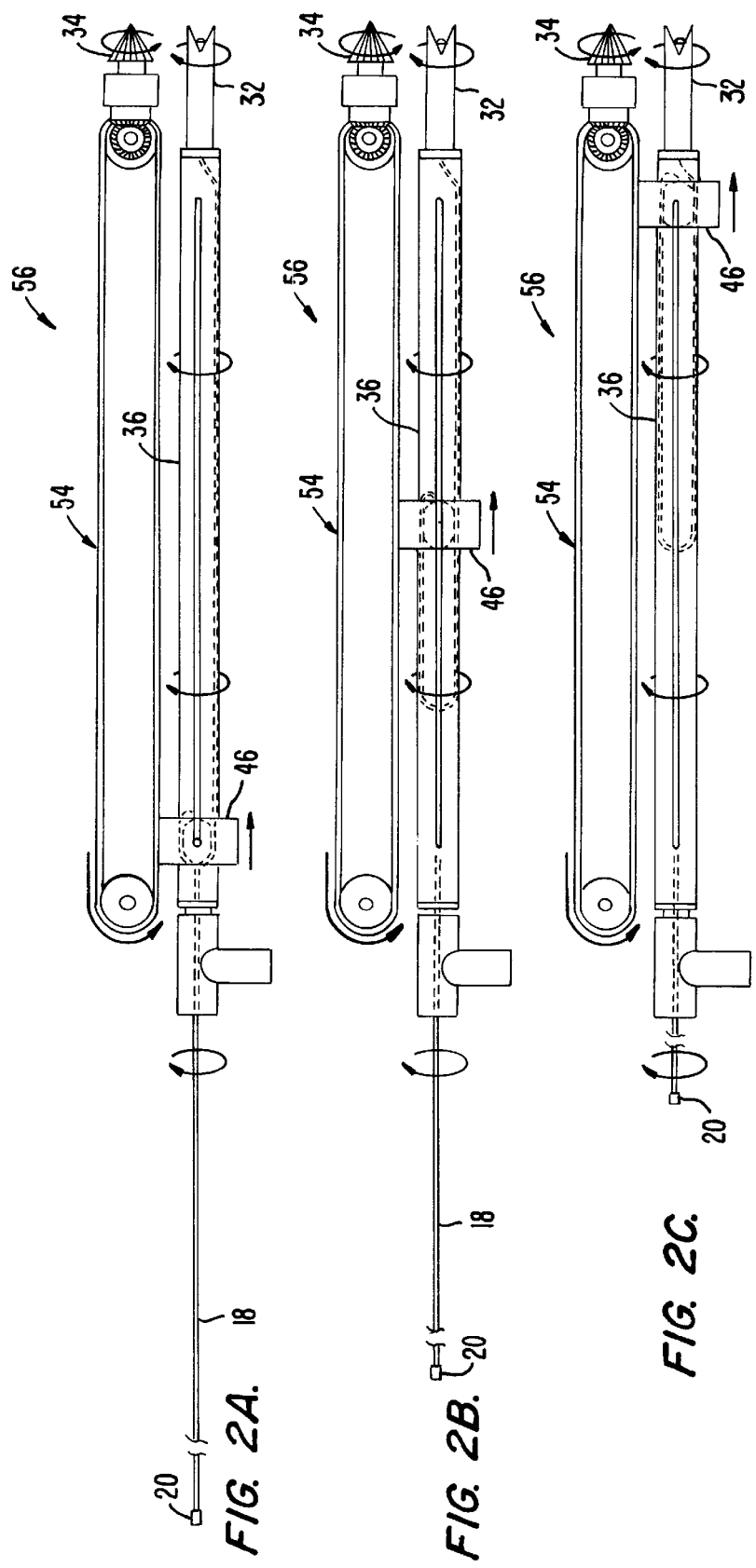

ROTATIONAL AND TRANSLATIONAL DRIVE COUPLING FOR CATHETER ASSEMBLY

CROSS-REFERENCES TO RELATED APPLICATIONS

This claims the benefit of U.S. Provisional Patent Application No. 60/146,609 filed Jul. 30, 1999 and having the same title.

This is related to U.S. patent application Ser. No. 09/167,178 filed Oct. 6, 1998 and entitled "Driveable Catheter System, now abandoned; U.S. patent application Ser. No. 09/317,778, filed May 24, 1999, and entitled Driveable Catheter System now U.S. Pat. No. 6,398,755; U.S. patent application Ser. No. 09/130,198, filed Aug. 5, 1998 and entitled "Automatic/Manual Longitudinal Position Translator and Rotary Drive System for Catheters" now U.S. Pat. No. 6,319,227; U.S. patent application Ser. No. 09/047,064, filed May 7, 1998 and entitled "Combined Motor Drive and Automatic Longitudinal Position Translator for Ultrasonic Imaging System" now U.S. Pat. No. 6,004,271; U.S. patent application Ser. No. 08/721,433 filed Sep. 27, 1996 and entitled "Catheter System and Drive Assembly Thereof" now U.S. Pat. No. 5,957,941; U.S. patent application Ser. No. 08/722,325 filed Sep. 27, 1996 and entitled "Device for Controlled Longitudinal Movement of an Operative Element Within a Catheter Sheath and Method" now U.S. Pat. No. 5,827,313; and U.S. Pat. No. 5,361,768, issued Nov. 8, 1994 and entitled "Automated Longitudinal Position Translator for Ultrasonic Positioning Probes, and Method of Using Same".

BACKGROUND OF THE INVENTION

The present invention relates generally to catheters systems. In particular, the present invention is directed to a drive coupling for a catheter assembly that provides for the controlled longitudinal movement of an elongate element—such as a rotatable catheter core with an operative element, for example an ultrasonic transducer or an optical fiber imaging device, at its distal end, or a drive cable with an arthrectomy cutter at its distal end—housed within a sheath positioned within a patient.

Arteriosclerosis, also known as atherosclerosis, is a common human ailment arising from the deposition of fatty-like substances, referred to as atheromas or plaque, on the walls of blood vessels. Such deposits occur in both peripheral blood vessels which feed the limbs of the body and the coronary vessels which feed the heart. When the deposits accumulate in localized regions of a blood vessel, stenosis, or narrowing of the vascular channel, occurs. Blood flow is restricted and the person's health is at serious risk.

Numerous approaches for reducing and removing such vascular deposits have been proposed, including balloon angioplasty where a balloon-tipped catheter is used to dilate a region of atheroma, and other devices that are pushed or pulled along or through a deposit, such as arthrectomy where a blade or cutting bit is used to sever and remove the atheroma, spark gap reduction in which an electrical spark burns through the plaque, laser angioplasty where laser energy is used to ablate at least a portion of the atheroma, and opening of vessels through the use of stents.

Two major difficulties in using such devices are maintaining a constant translational rate for the device and obtaining images of and information on the region of the blood vessel to be treated. Several imaging techniques have been proposed. Catheters incorporating mechanical rotation of ultrasonic transducers for imaging are disclosed in U.S. Pat. Nos. 4,794,931; 5,000,185; 5,049,130; and 5,024,234. These catheters scan in a plane normal to the catheter axis. Catheters employing phased array imaging systems are disclosed in U.S. Pat. Nos. 4,841,977 and 4,917,097. Catheters employing fiber optic imaging components are also known.

Generally deposits extend some longitudinal distance along the length of a vessel. To view different portions of the deposit a physician typically moves a handle attached to a proximal end of the imaging catheter along the vessel, for example, by pushing or pulling the catheter.

Imaging using computer-assisted reconstruction algorithms enables physicians to view a representation of the patient's interior intravascular structures in two or three dimensions (i.e., so-called three-dimensional or longitudinal view reconstruction). In this connection, image reconstruction algorithms typically employ data-averaging techniques which assume that the intravascular structure between an adjacent pair of data samples will simply be an average of each such data sample. Thus, the algorithms use graphical "fill in" techniques to depict a selected section of a patient's vascular system under investigation. Of course, if data samples are not sufficiently closely spaced, then lesions and/or other vessel abnormalities may in fact remain undetected (i.e., since they might lie between a pair of data samples and thereby be "masked" by the image reconstruction algorithms mentioned previously).

Even with the most skilled physician, it is practically impossible to manually exercise sufficiently slow constant rate longitudinal translation of the ultrasound imaging device (which thereby provides for a precisely known separation distance between adjacent data samples). In addition, with manual translation, the physician must manipulate the translation device while observing the conventional two-dimensional sectional images. This division of the physician's attention and difficulty in providing a sufficiently slow constant translation rate can result in some diagnostic information being missed. To minimize the risk that diagnostic information is missed, it is necessary to lengthen the imaging scan time which may be stressful to the patient. Similarly, it is difficult for physicians to manually control the translational rate of arthrectomy catheters and other interventional devices that are longitudinally advanced and retracted through blood vessel and other body lumens.

U.S. Pat. No. 5,485,486 discloses an ultrasound imaging transducer which is capable of being translated longitudinally within a section of a patient's vascular system at a precise constant rate through the use of a longitudinal translation assembly. The longitudinal translation assembly moves the entire rotary drive assembly to provide the desired longitudinal movement of the transducer. Such an ability enables a series of precisely separated data samples to be obtained thereby minimizing (if not eliminating) distorted and/or inaccurate reconstructions of the ultrasonically scanned vessel section (i.e., since a greater number of more closely spaced data samples can reliably be obtained). Also, such an assembly can be operated in a "hands-off" manner which allows the physician to devote his or her attention entirely to the real-time images with the assurance that all sections of the vessel are displayed. While such a longitudinal translation assembly can work well, it is relatively large, bulky and heavy; it is expensive; and it is cumbersome to set up, in part because the rotary drive and longitudinal translation assemblies are wrapped in separate sterile drapes or barriers (plastic bags) for sterility.

One of the disadvantages with some conventional pullback systems is separate modules are used to provide the rotational and translational movement. These modules require the use of sterile barriers about each. Also, some prior art pullback systems lack the capability to permit the user to manually translate the catheter core to preposition the operative element along the distal end of the catheter core.

SUMMARY OF THE INVENTION

The present invention is directed to a driven catheter system including rotational and translational drive coupling as part of a catheter assembly. The invention eliminates the need for a sled as is used with many conventional catheter pullback units. User set up is greatly simplified with the invention. The catheter assembly is typically a disposable unit and is thus supplied to the user in a sterile condition so only a single sterile drape about a motor drive unit is needed.

The driven catheter system includes broadly a driven catheter assembly coupled to a control unit. The driven catheter assembly includes the motor drive unit and the catheter assembly mounted thereto. The catheter assembly includes a catheter extending from the rotational and translational drive coupling. The catheter includes a sheath and a core slidably housed within the sheath, the proximal end of the sheath being mounted to the housing of the drive coupling. The drive coupling includes an elongate rotary drive element, defining a first longitudinal drive path, mounted to the housing for rotation about a longitudinal axis. A termination element couples the proximal end of the core to the rotary drive element for longitudinal movement along the first longitudinal drive path. The termination element is also mounted to the rotary drive element for of the termination element and the core therewith by the rotary drive element. A bearing has a first part coupled to the termination member. The bearing also has a second part, the first and second parts being freely rotatable relative to one another. A longitudinal driver is mounted to the housing and has a longitudinal drive element coupled to the second part of the bearing. The longitudinal drive element is movable along a second longitudinal drive path. Accordingly, rotation of the rotary drive element rotates the termination element and the proximal end of the core therewith about the longitudinal axis. Longitudinal movement of the longitudinal drive element translates the bearing parallel to the longitudinal drive path; this causes the termination element and the proximal end of the core therewith to be translated along the first longitudinal drive path.

The rotary drive element preferably has a hollow interior which defines the first longitudinal drive path. A slot, opening into the hollow interior, can be provided to be oriented parallel to the longitudinal drive path. The first part of the bearing, typically the inner race of the bearing, is preferably connected to the termination member through the slot. The longitudinal drive element could be provided by a number of different drive structures, such as a continuous belt, a lead screw or worm drive. In a preferred embodiment a continuous loop drive belt is used. The drive belt is driven through a drive pulley. The drive pulley is preferably driven through a pair of bevel gears. A flexible data/signal line, in the preferred embodiment, extends between the termination element at the proximal end of the core and a data/signal terminal carried by the housing of the drive coupling. The data/signal terminal may be a separate terminal but is preferably part of a dual data/signal-rotary drive connector. The dual connector provides the necessary data/signal connection and also the rotary drive connection for the rotary drive element.

The motor drive unit includes first and second rotary drive outputs which are coupled to the elongate rotary drive element and the longitudinal driver, respectively. The motor drive unit preferably includes first and second drive trains each having driving and driven ends. The driving ends terminate at the first and second rotary drive outputs. The second drive train couples the second rotary drive outputs with a drive source, typically an electric motor. A clutch-type element and a movement indicator, such as an optical encoder, may be used along the second drive train. The optical encoder is preferably positioned between the clutch type element and the second rotary drive output. Provision of the clutch-type element permits a user to physically disengage the longitudinal driver from the drive source so that the termination element and the core therewith can be manually translated within the sheath without the drag which would otherwise be created by the drive source. The preferred position of the movement indicator ensures that the longitudinal position of the core is continuously updated even when the core is being manually translated.

Other features and advantages of the present invention will appear from the following description in which the preferred embodiment has been set forth in detail in conjunction with the accompanying drawings.

BRIEF DESCRIPTION OF THE DRAWINGS

FIG. 1 is a simplified schematic view of a driven catheter system made according to the invention;

FIG. 2 is an enlarged, simplified top view of the operative components of the catheter assembly of FIG. 1;

FIGS. 2A–2C illustrate the catheter components of FIG. 2 during a pullback sequence during which the core is rotated and pulled back;

FIG. 3 is a simplified cross-sectional view taken along line 3—3 of FIG. 2; and;

FIG. 4 is a schematic diagram of the motor drive unit of FIG. 1.

DESCRIPTION OF THE SPECIFIC EMBODIMENTS

FIG. 1 illustrates a driven catheter system 2 made according to the invention. System 2 includes broadly a conventional control unit 4 coupled to a driven catheter assembly 6. Assembly 6 includes a motor drive unit 8 to which is coupled a catheter assembly 10. Motor drive unit 8 is a reusable unit and is enclosed within a sterile drape or bag 12; catheter assembly 10 is preferably supplied in a sterile condition and is mounted to motor drive unit 8 as will be discussed in more detail below.

Catheter assembly 10 includes an elongate, flexible catheter 14 having an outer sheath 16 and a flexible inner core 18. Core 18 is typically made of a suitable material, such as Nitinol, and carries an appropriate operative element, such as an ultrasonic transducer 20, at the distal end of core 18. Catheter 14 terminates at a hub 22, the hub mounted to the housing 24 of a rotational and translational drive coupling 26. Hub 22 includes a flush port 28 to permit the interior of sheath 16 to be purged of gases, typically air, by the introduction of saline or other fluid through to the flush port. An O-ring seal 30, see FIG. 2, is provided upstream of flush port 28. Core 18 passes though seal 30 with seal 30 preventing the passage of the saline or other flushing fluid into the interior of housing 24.

Drive coupling 26 will be discussed with reference to FIGS. 1–3. Drive coupling 26 includes first and second drive inputs 32 and 34. First drive input 32 is a dual input providing for both rotary mechanical drive and data/signal inputs. Both inputs 32, 34 are coupleable to rotary drive outputs from motor drive unit 8 as will be discussed below. Drive input 32 is directly connected to and rotates an elongate rotary drive element 36. Element 36 has a generally rectangular cross sectional shape with a hollow interior 38, see FIG. 3, and a pair of slots 40 extending along the length of element 36 parallel to the rotational axis 42 of element 36. Drive element 36 is supported within housing 24 by appropriate bearings, not shown, so that rotation of first drive input 32 rotates drive element 36 about axis 42.

The proximal end of core 18 extends into interior 38 and is secured to a core termination element 44. Core termination element 44 is sized to slide freely along interior 38 parallel to axis 42. Termination element 44 is sized so that it may not rotate freely within hollow interior 38 about axis 42.

Drive element 36 is surrounded by a bearing 46 having inner and out races 48, 50 which freely rotate relative to one another. Inner race 48 has a pair of inwardly extending longitudinal drive pins 52 which pass through slots 40 and engage core termination element 44. This permits drive element 36 and core termination element 44 therein to freely rotate about axis 42 while the longitudinal position of core termination element 44 is determined by the longitudinal position of bearing 46.

Outer race 50 of bearing 46 is coupled to a belt 54 of a longitudinal driver 56. Longitudinal driver 56 includes a drive pulley 58 adjacent to second drive input 34 and an idler pulley 60 adjacent to hub 22. Drive pulley 58 and idler pulley 60 are both mounted within housing 24 such that the inner reach 62 of belt 54 extends parallel to slot 40 and axis 42 and defines a second longitudinal drive path coextensive with inner reach 62. Drive pulley 58 is connected to second drive input 34 by a bevel gear pair 64. In the preferred embodiment a portion of the outer surface of outer race 50 of bearing 46 and the outer surface of belt 54 have complementarily-shaped teeth-like projections which provide the necessary engagement of bearing 46 and drive belt 54. Other connection elements, such as adhesives, clips, or threaded fasteners, could also be used.

First drive input 32 includes both a mechanical drive surface 66 and a data/signal connection 68. Connection 68 is coupled to a data/signal line 70 which extends to a proximal end of core 18 at core termination element 44. As suggested in FIGS. 2, 2A, 2B and 2C, line 70 is in the form of a service loop to accommodate the axial movement of core termination element within drive element 36.

Referring now primarily to FIGS. 2 and 4, rotator drive unit 8 is seen to include a body 72 from which first and second rotary drive outputs 74, 76 extend. First rotary drive output 74 includes both a rotary drive surface 78, which drivenly engages surface 66, and a data/signal connector 80, which engages a complementarily constructed connector 68. First and second drive inputs 32, 34 and first and second drive output 44, 46 are configured so that upon engagement of the connectors, sterility drape 12 is pierced by the connectors. Therefore separate holes typically need not be made in sterility drape 12 prior to the engagement of inputs 32, 34 with outputs 74, 76.

Motor drive unit 8 includes a rotary drive motor 82 and a translation drive motor 84 coupled to their respective first and second drive output 74, 76 by first and second drive trains 86, 88. First drive train 86 includes an optical encoder 90 used to provide the rotary position of first drive train 86 and a rotary transformer 92 used to couple control unit 4 to transducer 20 and to permit the passage of the data/signals between transducer 20 and control unit 4 through lines 93. Drive train 86 is similar to that disclosed in U.S. patent application Ser. No. 09/317,778 filed May 24, 1999, entitled Driveable Catheter System.

Drive train 88 includes a clutch 94 which is engaged when translation drive motor 84 is activated to cause longitudinal movement of core 18. Engagement of clutch 94 is achieved through the use of a solenoid 96 which acts to drive translation drive motor 84 to and from clutch 94 according to the actuation of the drive motor 84. An optical encoder 98, which provides data on the relative position of ultrasonic transducer 20 is located between clutch 94 and second rotary drive output 76. Accordingly, when translation drive motor 84 is off, which causes solenoid 96 to disengage clutch 94, manual movement of bearing 96, and thus of transducer 20, can occur and translational position information will continue to be monitored by optical encoder 98. This manual movement is achieved using a manual translation knob 100 extending outwardly from outer race 50 of bearing 46 through a slot 102 formed in housing 24 as shown in FIG. 1. A translation shut-off button 104 is shown in FIG. 3 extending from knob 100 so that whenever the user desires to manually translate transducer 20, depressing button 104 will cause translation drive motor 84 to stop and solenoid 96 to separate the clutch elements of clutch 94.

FIG. 1 indicates that body 72 of motor drive unit 8 includes a number of controls 106, such as a translation on off button and a rotary drive on off button, and a display 108 used to provide the relative translational position of transducer 20. Preferably display 108 can be set to zero at any time so that relative motion of transducer 20 from that zero position can be indicated in the display. Of course any inputs, controls and displays provide with motor drive unit 8 can be, and typically are, provided at control unit 4.

In use, catheter assembly 10 is typically provided as a sterile disposable unit. Catheter 14 is flushed through flush port 28 and catheter 10 is mounted to motor drive unit 8 through the engagement of first and second drive inputs 32, 34 with first and second outputs 74, 76. In a non-automated mode, that is with translation drive motor 84 not actuated, rotation of core 18 is initiated by pressing a suitable button at controls 106 or control unit 4 which actuates rotary drive motor 82. Once imaging core 20 is at a proper start position, display 108 can be zeroed and then manual translation knob 100 is grasped by the user and moved along slot 102 to cause transducer 20 to be laterally translated within sheath 16, typically in a pull back mode. See FIGS. 2A–2C. Automatic translation of transducer 20 takes place by the actuation of translation drive motor 84 which causes solenoid 96 to move drive motor 84 towards clutch 94 causing the engagement of the clutch and the automatic, controlled translation of bearing 46 and thus of core 18 and transducer 20 therewith, again typically in a pullback mode. Although imaging transducers are typically operated in a pullback mode, in appropriate cases they could be operated in a push mode. Also, when the operative element of core 18 is other than an imaging transducer, operation in a push instead of or in addition to a pull back mode may be useful or required. The pull back transducer scan ends when bearing 46 has reached its end of travel along slot 40 upon actuation of an appropriate button or after movement of a chosen distance. Whenever translation movement is interrupted solenoid 96 moves translation drive motor 84 thus disengaging clutch 94 to permit core 18 to be freely manually positioned by the operator while continuing to provide relative longitudinal position data though optical encoder 98.

Modification in variation can be made to the disclosed embodiment without departing from the subject invention as defined in the following claims. For example, it may be desirable to configure catheter assembly in a manner such that when mounted to motor drive unit 8, control unit 4 knows the identity of the type of catheter assembly being used. Bearing 46 may be constructed to permit free rotation of inner and outer races 48, 50 in only one rotary direction rather than in both rotary directions.

Any and all patents, applications and printed publications referred to are incorporated by reference.

What is claimed is:

1. A rotational and translational drive coupling for moving an inner member of a catheter comprising:
    a housing:
        an elongate rotary drive element, comprising a first longitudinal drive path, mounted to the housing for rotation about a longitudinal axis;
        an inner catheter member termination element mounted to the rotary drive element for:
            longitudinal movement, relative to the rotary drive element, along the first longitudinal drive path; and
            rotary motion with the rotary drive element;
        a termination member;
        a bearing having a first part coupled to the termination member and a second part, said first and second parts freely rotatable relative to one another in at least one rotary direction; and
        a longitudinal driver, mounted to the housing, having a longitudinal drive element coupled to the second part of the bearing and movable along a second longitudinal drive path;
        whereby rotation of the rotary drive element rotates the termination element about the longitudinal axis, and longitudinal movement of the longitudinal drive element translates the bearing parallel to the second longitudinal drive path, which in turn translates the termination element along the first longitudinal drive path.

2. The drive coupling according to claim 1 wherein the housing at least substantially totally encloses the rotary drive element.

3. The drive coupling according to claim 1 wherein the rotary drive element has a hollow interior defining the first longitudinal drive path.

4. The drive coupling according to claim 3 wherein the rotary drive element has first and second ends and a dual data/signal-rotary drive connector at the first end.

5. The drive coupling according to claim 4 further comprising a flexible data/signal line extending between the termination element and the dual connector.

6. The drive coupling according to claim 5 wherein the data/signal line extends from the termination element, towards the second end of the rotary drive element and then back towards the dual connector at the first end of the rotary drive element.

7. The drive coupling according to claim 3 wherein the rotary drive element has a slot opening into said hollow interior parallel to the first longitudinal drive path.

8. The drive coupling according to claim 7 wherein said first part of the bearing is coupled to the termination member by a connector extending through the slot.

9. The drive coupling according to claim 1 wherein the longitudinal drive element comprises a continuous belt.

10. The drive coupling according to claim 9 wherein the longitudinal driver comprises an idler pulley, a drive pulley and a bevel gear drive, the continuous belt engaging the idler and drive pulleys, the bevel gear drive including a first bevel gear directly driving the drive pulley.

11. The drive coupling according to claim 1 wherein the rotary drive element comprises a first rotary drive input and the longitudinal driver comprises a second rotary drive input, said longitudinal driver comprising a drive train coupling the second rotary drive input to the longitudinal drive element.

12. The drive coupling according to claim 11 wherein said drive train comprises first and second bevel gears.

13. The drive coupling according to claim 12 wherein the drive train comprises a drive pulley driven by the second bevel gear and the longitudinal drive element comprises an endless belt engaging the drive pulley.

14. A rotational and translational drive coupling for moving an inner member of a catheter comprising:
    a housing:
        an elongate rotary drive element, having a hollow interior defining a first longitudinal drive path, mounted within the housing for rotation about a longitudinal axis;
        an inner catheter member termination element mounted to the rotary drive element for:
            longitudinal movement, relative to the rotary drive element, along the first longitudinal drive path; and
            rotary motion with the rotary drive element;
        the rotary drive element having first and second ends and a dual data/signal-rotary drive connector at the first end;
        a termination element;
        a flexible data/signal line extending between the termination element and the dual connector, the data/signal line extending from the termination element, towards the second end of the rotary drive element and then back towards the dual connector at the first end of the rotary drive element;
        a bearing having a first part coupled to the termination member and a second part, said first and second parts freely rotatable relative to one another;
        a longitudinal driver, mounted to the housing, having a longitudinal drive element coupled to the second part of the bearing and movable along a second longitudinal drive path; and
        the rotary drive element having a slot opening into said hollow interior parallel to the first longitudinal drive path, said first part of the bearing being coupled to the termination member by a connector extending through the slot;
        whereby rotation of the rotary drive element rotates the termination element about the longitudinal axis, and longitudinal movement of the longitudinal drive element translates the bearing parallel to the second longitudinal drive path, which in turn translates the termination element along the first longitudinal drive path.

15. The drive coupling according to claim 14 wherein:
    the longitudinal drive element comprises a continuous belt; and
    the longitudinal driver comprises an idler pulley, a drive pulley and bevel gear drive, the continuous belt engaging the idler and drive pulleys, the bevel gear drive including a first bevel gear directly driving the drive pulley.

16. A driven catheter assembly comprising:
    a motor drive unit comprising first and second rotary drive outputs;

a catheter assembly comprising:
　a rotational and translational drive coupling comprising:
　　a housing:
　　　first and second rotary drive inputs supported by the housing and drivenly coupled to the first and second rotary drive outputs;
　　　a catheter comprising an outer sheath on an inner member movably housed within the sheath, the outer sheath extending from the housing;
　　　means for drivingly coupling the inner member to the first and second rotary drive inputs so that rotation of the first and second rotary drive outputs rotates and translates the inner member, respectively.

17. The catheter system according to claim 16 wherein the motor drive unit comprises first and second drive trains each having driving and driven ends, said driving ends terminating at the first and second rotary drive outputs, respectively.

18. The catheter system according to claim 17 further comprising a drive source at the driven end of the second drive train, a clutch along the second drive train between the drive source and the second rotary drive output, and a movement indicator along the second drive train between the clutch and the second rotary drive output.

19. The catheter system according to claim 16 further comprising a flexible, drapeable sterile wrap enclosing the motor drive unit, said first and second rotary drive outputs and inputs comprising bag-piercing drive elements which effectively pierce said sterile wrap when said first and second rotary drive outputs and inputs engage.

20. A method for using a driven catheter system comprising;
　selecting a catheter assembly, the catheter assembly comprising a rotatable and translatable drive coupling from which a catheter extends, the catheter comprising a sheath housing a rotatable and translatable core, the core having a proximal end and a distal end;
　mounting first and second drive inputs and a first data/signal connector of the drive coupling to first and second drive outputs and a second data/signal connector of a motor drive unit, the motor drive unit comprising first and second drive motors which rotate the first and second drive outputs causing the first and second drive inputs to rotate;
　operating the first drive motor which rotates a rotary drive element of the drive coupling about an axis, the proximal end of the core coupled to the rotary drive element to rotate with the rotary drive element thereby causing the proximal end of the core to rotate about the axis and the core to rotate within the sheath; and
　operating the second drive motor which drives a longitudinal driver of the drive coupling, the longitudinal driver operably coupling the second drive input to the proximal end of the core so to move the proximal end of the core along the axis relative to the rotary drive element and to translate the core within the sheath, the second drive motor operating step being carried out at least partially simultaneously with the first drive motor operating step.

21. The method according to claim 20 further comprising flushing the catheter of the assembly with a flushing fluid.

22. The method according to claim 20 wherein the first drive input and the first data/signal connector are coaxially mounted to the first drive output and the second data/signal connector during the mounting step.

23. The method according to claim 20 further comprising monitoring the longitudinal position of the distal end of the core relative to the sheath.

24. The method according to claim 23 further comprising the step of decoupling the second drive motor from the longitudinal driver and manually longitudinally moving the proximal end of the core while continuing to monitor the longitudinal position of the distal end of the core relative to the sheath.

\* \* \* \* \*